United States Patent

Nakada et al.

Patent Number: 4,542,110
Date of Patent: Sep. 17, 1985

[54] PROCESS FOR PRODUCING ZIRCONIUM OXIDE SINTERED BODY

[75] Inventors: Takao Nakada, Hitachi; Mamoru Kamimura, Katsuta; Toranosuke Ashizawa, Hitachi, all of Japan

[73] Assignee: Hitachi Chemical Company, Ltd., Tokyo, Japan

[21] Appl. No.: 683,679

[22] Filed: Dec. 19, 1984

Related U.S. Application Data

[63] Continuation of Ser. No. 498,065, May 25, 1983, abandoned.

[30] Foreign Application Priority Data

Jun. 8, 1982 [JP] Japan ................................ 57-98293

[51] Int. Cl.$^4$ ............................................. C04B 35/48
[52] U.S. Cl. .................................... 501/103; 204/424; 264/66; 501/105; 501/152
[58] Field of Search ............... 204/424; 501/103, 105, 501/152; 264/56, 66, 65

[56] References Cited

U.S. PATENT DOCUMENTS

| | | | |
|---|---|---|---|
| 4,193,857 | 3/1980 | Bannister et al. | 204/426 |
| 4,219,359 | 8/1980 | Miwa et al. | 501/152 |
| 4,266,979 | 5/1981 | Miyoshi et al. | 501/103 |
| 4,316,964 | 2/1982 | Lange et al. | 501/105 |
| 4,328,294 | 5/1982 | Tanaka et al. | 501/103 |
| 4,328,296 | 5/1982 | Tanaka et al. | 501/103 |
| 4,465,778 | 8/1984 | Brook et al. | 501/152 |

FOREIGN PATENT DOCUMENTS

| | | | |
|---|---|---|---|
| 54-25523 | 8/1979 | Japan . | |
| 54-150191 | 11/1979 | Japan | 204/424 |
| 55-67647 | 5/1980 | Japan | 204/424 |

OTHER PUBLICATIONS

Andreeva, A. B. et al., "A Highly Refractory Material Based on Zirconia Stabilized with Yttrium and Aluminum Oxides"-Refractories-vol. 14, No. 3-4, pp. 244-246, Mar.-Apr. 1973 (publ. Jan. 1974).

Primary Examiner—Helen M. McCarthy
Attorney, Agent, or Firm—Antonelli, Terry & Wands

[57] ABSTRACT

A zirconium oxide sintered body for an oxygen concentration sensor is produced by mixing 87.5 to 91.0% by weight of zirconium oxide powder, 8.5 to 12.3% by weight of yttrium oxide powder, 0.5% by weight or less of silicon oxide and 0.2 to 1.0% by weight of aluminum oxide, drying the resulting mixture, followed by sintering so as to make the cubic phase content in crystal phase of the resulting sintered body at ordinary temperatures 95% by weight or more. Said zirconium oxide sintered body is excellent in mechanical strength, thermal shock and ionic conductivity and can be used stably for a long period of time.

6 Claims, 1 Drawing Figure

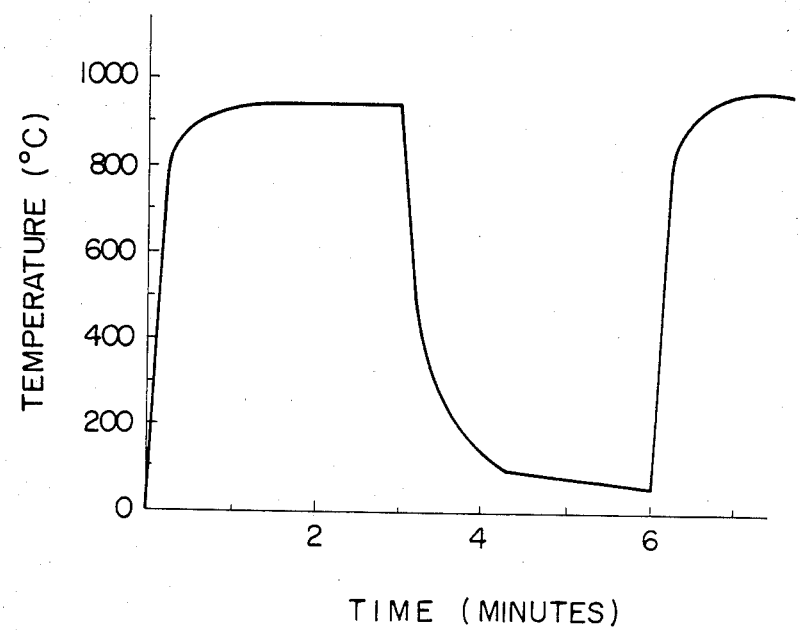

PROCESS FOR PRODUCING ZIRCONIUM OXIDE SINTERED BODY

This is a continuation of application Ser. No. 498,065, filed May 25, 1983, now abandoned.

This invention relates to a process for producing a zirconium oxide sintered body used for an oxygen concentration sensor for measuring the concentration of oxygen.

Methods of detecting the partial pressure of oxygen by use of a zirconium oxide sintered body enable a very accurate value to be obtained in an instant and by a simple procedure, and hence have become the main current of methods of measuring the partial pressure of oxygen, and by taking advantage of this they are often used for the control of combustion, the detection of oxygen deficit and the like. However, in such detection methods, the oxygen ion conductivity of zirconium oxide is used, so that in usual, zirconium oxide should be heated to 700° to 800° C. Therefore, zirconium oxide to be used should not deteriorate at high temperatures and should be resistant to heat shock in the raising and lowering of temperature. However, when a zirconium oxide sintered body having a good ionic conductivity is produced and then subjected to measurement, it has a low mechanical strength and a high coefficient of thermal expansion, and therefore it tends to be destroyed by heat shock. In order to increase the mechanical strength of zirconium oxide, there has been proposed the production of a partially stabilized zirconium sintered body by the reduction of the amount of yttrium oxide added. When the amount of yttrium oxide added is reduced, the resulting sintered body has increased mechanical strength and a lowered coefficient of thermal expansion and hence is resistant to heat shock, however it is lowered in ionic conductivity required of a material for a sensor, and moreover it has an unstable crystal structure and hence is poor in long-term stability at high temperatures, so that it has disadvantages in practical use such as the occurence of cracks during its use, and the like.

In order to obtain a zirconium oxide sintered body resistant to heat shock, it is usually believed to be advisable to include therein a large amount of a monoclinic phase. In practice, even when a zirconium oxide sintered body containing 6.5% by weight of yttrium oxide and 40% by weight of a monoclinic phase is produced, and put in water immediately after heating at 800° C., it is not destroyed. However, when repeatedly heated from ordinary temperatures to 800° C., it decreases in mechanical strength sharply, and therefore including therein a large amount of monoclinic phase has found to be ineffective.

On the other hand, a process for producing a stabilized high-density sintered body of zirconia has been disclosed in Japanese Patent Appln Kokoku (Post-Exam Publn) No. 25,523/79. According to said reference, there has been proposed a process for producing a high-density stabilized sintered body of zirconia, comprising adding aqueous ammonia to an aqueous solution of a water-soluble zirconium salt in which are dissolved at least one first component selected from soluble salts or oxides of calcium, magnesium, yttrium, titanium and cerium and at least one second component selected from soluble salts or oxides of bismuth, copper, tin, aluminum and iron, thereby forming a precipitate of a mixed hydroxide dispersing the precipitate into an organic solvent, subjecting the resulting dispersion to distillation until the boiling point reaches at least 100° C., separating and then drying the precipitate, calcining it at a temperature equal to or higher than 150° C., molding the thus obained fine powder, and then sintering it at 1,500° to 1,700° C., which is characterized in that the amounts of the aforesaid first and second components added are adjusted so that the first and second components are present in the final sintered body in amounts of 3 to 15% by weight and 0.1 to 0.6% by weight, respectively, in terms of the respective oxides. However, this process is disadvantageous, for example, in that the material cost is high because water-soluble materials are used; that a tank for forming the precipitate, an apparatus for recovering (filter press or the like) the precipitate, or the like is needed; that the process is long and complicated and the production cost is high; and that although the obtained powder is easy to sinter, it is highly bulky and has a large volume shrinkage due to sintering, so that it tends to cause cracks, deformation or the like with the progress of vitrification, and hence is difficult to handle.

An object of the present invention is to provide a process for efficiently producing a zirconium oxide sintered body excellent in mechanical strength and thermal shock resistance by a manageable process, which has overcome the disadvantages of such a conventional process as described above.

The present invention provides a process for producing a zirconium oxide sintered body whose crystal phase at ordinary temperatures contains 95% by weight or more of a cubic phase, which comprises mixing 87.5 to 91.0% by weight of zirconium oxide powder, 8.5 to 12.3% by weight of yttrium oxide powder, 0.5% by weight or less of silicon oxide and 0.2 to 1.0% by weight of aluminum oxide, drying the resulting mixture, and then sintering the mixture.

The accompanying drawing is a graph showing a relationship between time and temperature in a heat cycle test.

According to the process of this invention, a zirconium oxide sintered body is produced by adding yttrium oxide in a minimal amount in which zirconium oxide crystals are almost completely stabilized, and dispersing the yttrium oxide uniformly; therefore the obtained sintered body is not destroyed even when rapidly heated from ordinary temperatures to 800° C. and rapidly cooled from 800° C. to ordinary temperatures, and even after this procedure is repeated 500 cycles, the mechanical strength is measured and found to remain unchanged and the ionic conductivity is not lowered but retains as high as a value of 800 $\Omega^{-1} cm^{-1}$ at 700° C.

The starting materials used in this invention may be commercially available oxide powders, which need not be subjected to a special chemical treatment or the like. When yttrium oxide is mixed, wet ball mill blending is suitable. It is desirable that the resulting mixture is dried and then heat-treated at a temperature equal to or higher than 1,300° C., preferably from 1,300° C. to 1,500° C. for 10 to 120 minutes, more preferably at a temperature of 1,400° C. for 60 minutes.

In this invention, in order to adjust the cubic phase content in crystal phase of the zirconium oxide sintered body to 95% by weight or more, it is sufficient, for example, to repeat plural times the blending and the heat-treatment step, and the adjustment can also be achieved, for example, by carrying out the blending treatment for a long time to disperse yttrium oxide into zirconium oxide as uniformly as possible and sintering these powders.

The particle sizes of the oxide powders as the starting materials are not critical. It is sufficient that the size of particles obtained by mixing the oxide powders and grinding the resulting mixture is 1 μm or less on an average, and the content of particles having a size of 0.5 μm or less is preferably 40% by weight or more, more preferably 52% by weight or more.

The sintering is preferably conducted in air or a neutral (e.g., nitrogen) atmosphere at a temperature of 1,500° to 1,700° C.

The zirconium oxide sintered body obtained by the process of this invention should contain 87.5 to 91.0% by weight, preferably 88.5 to 90.0% by weight of zirconium oxide, 8.5 to 12.3% by weight, preferably 9.2 to 10.7% by weight of yttrium oxide, 0.5% by weight or less of silicon oxide and 0.2 to 1.0% by weight, preferably 0.4 to 0.8% by weight of aluminum oxide; and its crystal phase at ordinary temperatures should contain 95% or more of a cubic phase. When the amount of the zirconium oxide is less than 87.5% by weight, or when the amount of the yttrium oxide exceeds 12.3% by weight, the resulting sintered body has a lowered mechanical strength and has a disadvantage in that it is destroyed merely by rapid heating. When the amount of the zirconium oxide exceeds 91.0% by weight or when the amount of the yttrium oxide is less than 8.5% by weight, the content of monoclinic zirconium oxide crystals becomes too high and the reduction of the mechanical strength in a heat cycle test becomes large. When the amount of the aluminum oxide is less than 0.2% by weight, the sintering temperature should be adjusted to 1,700° C. or higher, so that the sintering cost becomes high. On the other hand, when the amount of the aluminum oxide exceeds 1.0% by weight, the ionic conductivity is lowered. When the total amount of the silicon oxide contained as an impurity in the starting materials exceeds 0.5% by weight, the ionic conductivity is similarly lowered.

When the ionic conductivity is thus lowered, the areas of electrodes should be increased in order to obtain a necessary output, and hence the used amount of platinum as a material for the electrodes increases sharply, so that a disadvantage of a high cost is brought about. When the cubic phase content is less than 95% by weight, repeated heating from ordinary temperatures of 800° C. sharply lowers the mechanical strength. Therefore, it is not preferable.

In this invention, it is sufficient that the cubic phase content in the crystal phase at ordinary temperatures is 95% by weight or more. It is preferably 97% by weight because at this content, the reliability is improved. It is more preferably 100% by weight because at this content, the reliability is further improved.

This invention is explained below referring to Examples.

EXAMPLES 1 TO 5 AND COMPARATIVE EXAMPLES 1 TO 10

Zirconium oxide powder (EP Grade, a trade name, manufactured by Daiichi Kigenso Kagaku Co., Ltd.) and yttrium oxide powder (99.9% purity, manufactured by Shin-etsu Chemical Industry Co., Ltd.) were weighed in each proportion shown in Table 1 and subjected to wet blending for 24 hours by using zirconium oxide balls and a rubber-lined ball mill. The resulting mixture was dried and then heat-treated at 1,350° C. for 2 hours, and the thus treated powder was repeatedly subjected to wet blending, drying and heat treatment in the same manner as described above to obtain zirconium oxide powder containing yttrium oxide dispersed therein.

Next, to the thus obtained powder were added aluminum oxide (AI-160, a trade name, manufactured by Showa Keikinzoku K.K.) and silicon oxide (prepared by grinding reagent grade (first class) and adjusting the average particle size to 1.0 μm) in each proportion shown in Table 1, and 2 parts by weight of a 5% aqueous polyvinyl alcohol (PVA) solution was further added, after which they were subjected to wet blending for 24 hours, and the resulting mixture was dried by means of a spray drier and granulated. The thus granulated powder was formed into a 10×10×50 mm plate under a forming pressure of 1 ton/cm² and then sintered at each temperature shown in Table 1 to obtain a zirconium oxide sintered body.

Next, the thus obtained zirconium oxide ceramic or porcelain was placed in a testing apparatus undergoing temperature variation as shown in the accompanying drawing, and its flexural strength after a 500 cycles heating test was measured and was considered as an indication of its deterioration. As a result, it was confirmed that as shown in Table 1, the composition and cubic phase content of the porcelain were important factors.

TABLE 1

| Sample No. | Zirconium oxide (wt. %) | Yttrium oxide (wt. %) | Number of times of blending and heat treatment of mixture (times) | Aluminum oxide (wt. %) | Silicon oxide (wt. %) | Sintering temperature (°C.) |
|---|---|---|---|---|---|---|
| Comparative Example 1 | 86.0 | 13.0 | 1 | 0.5 | 0.5 | 1650 |
| Comparative Example 2 | " | " | 2 | " | " | " |
| Comparative Example 3 | 87.0 | 12.6 | 1 | 0.4 | 0 | 1660 |
| Comparative Example 4 | " | " | 3 | " | " | " |
| Comparative Example 5 | 87.8 | 12.0 | 1 | 0.2 | " | 1700 |
| Example 1 | " | " | 2 | " | " | " |
| Comparative Example 6 | 89.0 | 10.1 | 1 | 0.4 | 0.5 | 1630 |
| Example 2 | " | " | 3 | " | " | " |
| Example 3 | " | " | 3 | 0.9 | 0 | " |
| Comparative | 90.0 | 9.2 | 1 | 0.8 | " | " |

TABLE 1-continued

| Sample No. | | | | | | |
|---|---|---|---|---|---|---|
| Example 7 Comparative Example 8 | " | " | 3 | " | " | " |
| Example 4 Comparative Example 9 | 90.8 | 9.0 | 5 1 | 0.2 | " | " 1700 |
| Example 5 Comparative Example 10 | 91.5 | 8.0 | 4 4 | 0.5 | " | " 1600 |

| Sample No. | Duration of maintenance of the highest temperature (hr.) | Cubic phase (%) | Initial strength (kg/mm²) | Strength after 500 cycles (kg/mm²) | Remark |
|---|---|---|---|---|---|
| Comparative Example 1 | 2 | 97 | 20 | 18 | 2/5 Destroyed at the time of test |
| Comparative Example 2 | " | 100 | 21 | 20 | 4/5 Destroyed |
| Comparative Example 3 | " | 92 | 22 | 10 | |
| Comparative Example 4 | " | 100 | 24 | 22 | 2/5 Destroyed at the time of test |
| Comparative Example 5 | " | 77 | 24 | 6 | |
| Example 1 | " | 95 | 24 | 20 | |
| Comparative Example 6 | " | 70 | 28 | 5 | |
| Example 2 | " | 97 | 25 | 20 | |
| Example 3 | " | 100 | 24 | 22 | |
| Comparative Example 7 | " | 65 | 33 | 3 | |
| Comparative Example 8 | " | 92 | 27 | 12 | |
| Example 4 | " | 100 | 25 | 22 | |
| Comparative Example 9 | " | 48 | 37 | 3 | |
| Example 5 | " | 98 | 27 | 22 | |
| Comparative Example 10 | " | 87 | 35 | 7 | |

Since the zirconium oxide sintered body obtained by the process of this invention contains 87.5 to 91.0% by weight of zirconium oxide, 8.5 to 12.3% by weight of yttrium oxide, 0.5% by weight or less of silicon oxide and 0.2 to 1.0% by weight of aluminum oxide and its crystal phase at ordinary temperatures contains 95% by weight or more of a cubic phase, it is not lowered in mechanical strength and ionic conductivity by a heat cycle and hence can stably be used for a long time. Further, since it has a high ionic conductivity, a stable output can be obtained even when the areas of electrodes are small, and the electrodes can be made small, so that the amount of platinum used as a material for the electrodes can be reduced.

What is claimed is:

1. A process for producing a zirconium oxide sintered body, which comprises wet blending 87.5 to 91.0% by weight of zirconium oxide powder to grind mixture of oxide powders, and 8.5 to 12.3% by weight of yttrium oxide powder, drying the resulting mixture, and subjecting the dried mixture to heat treatment at a temperature higher than 1,300° C. and below sintering temperature, wherein the average particle size of the mixture of the oxide powders after grinding is 1 um or less; mixing the heat-treated mixture with 0.5% by weight or less of silicon oxide and 0.2 to 1.0% by weight of aluminum oxide, and then sintering the mixture to obtain 95% by weight or more of a cubic phase in a crystal phase at ordinary temperatures.

2. A process according to claim 1, wherein the sintering is conducted in air or a neutral atmosphere at 1,500° to 1,700° C.

3. A process according to claim 1, wherein the blending step, drying step and the heat treatment step are repeated 2 times or more.

4. A process according to claim 2, wherein the resulting mixture is heat treated from 1,300° to 1,500° C. for 10 to 120 minutes.

5. A process according to claim 4, wherein the mixing of the mixture containing the heat-treated mixture, silicon oxide and aluminum oxide is effected by wet blending and thereafter drying this mixture prior to the sintering step.

6. A process according to claim 5, wherein wet-blending of the mixture is carried out for a period of 24 hours.

* * * * *